(12) United States Patent
Mathison (10) Patent No.: US 7,998,196 B2
(45) Date of Patent: Aug. 16, 2011

(54) REPLACEMENT HEART VALVE, VALVE HOLDER AND METHODS OF MAKING AND USING SAME

(75) Inventor: Megumi Mathison, Atlanta, GA (US)

(73) Assignee: Saint Joseph's Translational Research Institute, Inc., Atlanta, GA (US)

( * ) Notice: Subject to any disclaimer, the term of this patent is extended or adjusted under 35 U.S.C. 154(b) by 90 days.

(21) Appl. No.: 12/106,591

(22) Filed: Apr. 21, 2008

(65) Prior Publication Data
US 2008/0262608 A1    Oct. 23, 2008

Related U.S. Application Data

(60) Provisional application No. 60/925,822, filed on Apr. 23, 2007.

(51) Int. Cl.
*A61F 2/06* (2006.01)
(52) U.S. Cl. .................................. 623/2.12; 623/2.1
(58) Field of Classification Search ............ 623/2.1, 623/2.11, 2.12, 2.17, 2.19
See application file for complete search history.

(56) References Cited

U.S. PATENT DOCUMENTS

| | | | |
|---|---|---|---|
| 4,702,250 A * | 10/1987 | Ovil et al. | 606/148 |
| 7,331,993 B2 * | 2/2008 | White | 623/2.12 |
| 2005/0137682 A1 | 6/2005 | Justino | |
| 2005/0240262 A1 | 10/2005 | White | |
| 2008/0249620 A1 * | 10/2008 | Bicer | 623/2.11 |

FOREIGN PATENT DOCUMENTS

| WO | 2005011534 A1 | 2/2005 |
|---|---|---|
| WO | 2007038540 A1 | 4/2007 |

OTHER PUBLICATIONS

Park, Joong Wha et al., "Small Intestinal Submucosa Covered Explandable Z Stents for Treatment of Tracheal Injury: An Experimental Pilot Study in Swine," JVIR 2000; pp. 1325-1330, vol. 11.

* cited by examiner

*Primary Examiner* — David Isabella
*Assistant Examiner* — Seema Swaminathan
(74) *Attorney, Agent, or Firm* — Tim Tingkang Xia; Morris, Manning & Martin, LLP (57) ABSTRACT

A replacement heart valve device usable in a medical procedure in relation in heart valve replacement of a patient. In one embodiment, the replacement heart valve device includes a heart valve holder or conduit holder formed in the form of a cylindrical tube having a longitudinal cut substantially extending from one end to the other end of the cylindrical tube, and a conduit formed with a tubular segment of an elastic material. The conduit is mountable onto the heart valve holder or conduit holder or self-expanding stent. In one embodiment, at least a portion of the conduit is formed with a single layer of the elastic material. In another embodiment, at least a portion of the conduit is formed with two layers of the elastic material.

19 Claims, 9 Drawing Sheets

FIG. 1E (Optional)

REPLACEMENT HEART VALVE, VALVE HOLDER AND METHODS OF MAKING AND USING SAME

CROSS-REFERENCE TO RELATED PATENT APPLICATION

This application claims the benefit, pursuant to 35 U.S.C. §119(e), of U.S. provisional patent application Ser. No. 60/925,822, filed Apr. 23, 2007, entitled "REPLACEMENT HEART VALVE, VALVE HOLDER AND METHODS OF MAKING AND USING SAME," by Megumi Mathison, which is incorporated herein by reference in its entirety.

FIELD OF THE INVENTION

This invention relates to a replacement heart valve, and more particularly relates to a replacement heart valve formed with a tubular segment of an elastic material for replacement of a defective heart valve of a human or animal.

BACKGROUND OF THE INVENTION

There are four valves in the heart that serve to direct blood flow through the two sides of the heart. On the left (systemic) side of the heart are: (1) the mitral valve, located between the left atrium and the left ventricle, and (2) the aortic valve, located between the left ventricle and the aorta. These two heart valves direct oxygenated blood from the lungs through the left side of the heart and into the aorta for distribution to the body. On the right (pulmonary) side of the heart are: (1) the tricuspid valve, located between the right atrium and the right ventricle, and (2) the pulmonary valve, located between the night ventricle and the pulmonary artery. These two heart valves direct de-oxygenated blood from the body through the right side of the heart and into the pulmonary artery for distribution to the lungs, where the blood becomes re-oxygenated in order to begin the circuit anew.

All four of these heart valves are passive structures in that they do not themselves expend any energy and do not perform any active contractile function. They consist of moveable "leaflets" that open and close in response to differential pressures on either side of the valve. The mitral and tricuspid valves are referred to as "atrioventricular valves" because they are situated between an atrium and ventricle on each side of the heart. The mitral valve has two leaflets and the tricuspid valve has three. The aortic and pulmonary valves are referred to as "semilunar valves" because of the unique appearance of their leaflets, which are shaped somewhat like a half-moon and are more aptly termed "cusps". The aortic and pulmonary valves each have three cusps.

Heart valves may exhibit abnormal anatomy and function as a result of congenital or acquired valve disease. Congenital valve abnormalities may be well-tolerated for many years only to develop a life-threatening problem in an elderly patient, or may be so severe that emergency surgery is required within the first few hours of life. Acquired valve disease may result from causes such as rheumatic fever, degenerative disorders of the valve tissue, bacterial or fungal infections, and trauma.

Since heart valves are passive structures that simply open and close in response to differential pressures on either side of the particular valve, the problems that can develop with heart valves can be classified into two categories: (1) stenosis, in which a valve does not open properly, and (2) insufficiency (also called regurgitation), in which a valve does not close properly. Stenosis and insufficiency may occur concomitantly in the same valve or in different valves. Both of these abnormalities increase the workload placed on the heart. The severity of this increased stress on the heart and the patient, and the heart's ability to adapt to it, determine whether the abnormal valve will have to be surgically replaced (or, in some cases, repaired).

Valve repair and valve replacement surgery is described and illustrated in numerous books and articles, and a number of options, including artificial mechanical valves and artificial tissue valves, are currently available. However, the currently available options cannot duplicate the advantages of native (natural) heart valves. Some of the available mechanical valves tend to be very durable, but are problematic in that they are thrombogenic and exhibit relatively poor hemodynamic properties. Some of the available artificial tissue valves may have relatively low thrombogenicity, but lack durability. Additionally, even these artificial tissue valves often do not exhibit hemodynamic properties that approach the advantageous hemodynamic performance of a native valve. Some artificial tissue valves attempt to copy the form of native heart valves. Such artificial tissue valves still fall short in durability and in hemodynamic performance.

Moreover, external valve conduits for right ventricular outflow tract (RVOT) have markedly extended the range of complex congenital heart defects that can be repaired: pulmonary atresia, complex tetralogy of Fallot, double outlet right or left ventricle with pulmonary stenosis, truncus arteriosus, transposition of great arteries with ventricular septal defect and pulmonary stenosis, and other complex forms of congenital heart disease.

Although the immediate and long-term survival of patients is gratifying, all conduits deteriorate, requiring the need to have close, constant follow-up. A large proportion, if not all, will have to be replaced at least once during the patient's lifetime. In the case of children, multiple surgeries are often required, which put the child at risk and can be physically and emotionally draining for the child and his or her family. The development and use of improved substitutes for RVOT conduits could reduce the need for multiple surgeries for children with various congenital heart diseases. Tissue-engineered RVOT conduits could significantly improve the quality of life for such children while decreasing the associated medical costs.

Therefore, a heretofore unaddressed need still exists in the art to address the aforementioned deficiencies and inadequacies.

SUMMARY OF THE INVENTION

The present invention, in one aspect, relates to a method of making a replacement heart valve that is implantable to a patient. In one embodiment, the method has the step of providing a tubular segment of an elastic material having a first end portion and an opposite, second end portion, an interior surface, an exterior surface and a diameter $d_1$. The elastic material is one of an intestinal tissue obtained from a mammalian abdomen, a man-made bio-compatible tissue, and a polymeric material. For example, the intestinal tissue can be extracted from the patient who receives the replacement heart valve. Alternatively, the intestinal tissue can be extracted from other human beings and/or animals.

The method also has the steps of folding the first end portion inside-out towards to the second end portion such that the first end of the tubular segment reaches a position on the exterior surface and the tubular segment has a new first end, where the first end and the new first end define a new first end portion with an axial distance $d_2$ that is substantially equals to $d_1$, and forming a plurality of cusps on the new first end portion axially. In one embodiment, the step of forming a plurality of cusps on the new first end portion axially has the step of forming three cusps by sewing along three lines on the new first end portion longitudinally, where the three cusps are formed substantially parallel to each other and substantially apart from each other in 120°, as seen from a longitudinal, central axis of the tubular segment. The sewing in one embodiment is performed with one or more threads of 7-0 or 6-0 prolene.

Furthermore, the method has the steps of inverting the tubular segment inside out so that the exterior surface of the tubular segment and the interior surface of the tubular segment exchange their geometric positions to form a replacement heart valve that has a conduit at least partially with a single layer of the elastic material.

Moreover, the method can be practiced to create a replacement heart valve that has a conduit at least partially with two layers of the elastic material from the replacement heart valve that has a conduit at least partially with a single layer of the elastic material. In one embodiment, the second end portion is folded inside-out towards to the new first end such that the second end of the tubular segment substantially reaches the new first end. As a result, a conduit at least partially with two layers of the elastic material is formed with the new first end and a new second end, where the new first end and the new second end define an axial distance $d_3$ that is no smaller than either of $d_1$ and $d_2$.

In operation, each of a replacement heart valve that has a conduit at least partially with a single layer of the elastic material and a conduit at least partially with two layers of the elastic material can be mounted onto a heart valve holder or conduit holder.

In another aspect, the present invention relates to a replacement heart valve made according to the method as disclosed above.

In yet another aspect, the present invention relates to a replacement heart valve implantable in a patient. In one embodiment, a replacement heart valve includes a conduit formed with a tubular segment of an elastic material, wherein the conduit has a first end portion and an opposite, second end portion, and a plurality of cusps formed axially extending inwardly from one of the first and second end portions. In one embodiment, the conduit is formed at least partially with a single layer of the elastic material. In another embodiment, the conduit is formed at least partially with two layers of the elastic material.

In one embodiment, the elastic material is one of an intestinal tissue obtained from a mammalian abdomen, a man-made bio-compatible tissue, and a polymeric material. The intestinal tissue can be extracted from a patient who receives the replacement heart valve.

In one embodiment, the plurality of cusps comprises three cusps, wherein the three cusps are formed substantially parallel to each other and substantially apart from each other in 120°, as seen from a longitudinal, central axis of the conduit.

In a further aspect, the present invention relates to a method of making a heart valve holder or conduit holder usable for mounting a conduit formed with an elastic material. In one embodiment, the method has the steps of providing a tube with a first end portion and an opposite, second end portion, forming a cut longitudinally on the tube, and forming a plurality of holes on the tube. The tube is made from a bio-compatible material. In one embodiment, the tube is made from an at least partially transparent material. For example, the tube can be made from a plastic.

The step of forming the cut longitudinally on the tube has the step of forming the cut substantially extending from the first end to the second end, or vice versa.

Additionally, the method also includes the step of forming a plurality of round edges around the first end and the second end, respectively, after the cut is formed.

In one embodiment, the step of forming the plurality of holes on the tube has the step of forming three pairs of holes, respectively, where the three pairs of holes are formed substantially parallel to each other and substantially apart from each other in 120°, as seen from a longitudinal, central axis, A, of the tube.

Furthermore, when a conduit formed with an elastic material is mounted to the heart valve holder or conduit holder, the method further has the steps of guiding a thread through each of the three pair of holes, and tying two corresponding threads from each side for each of the three pair of holes.

In yet a further aspect, the present invention relates to a heart valve holder or conduit holder made according to the method as disclosed above.

In one aspect, the present invention relates to a heart valve holder or conduit holder. In one embodiment, the heart valve holder or conduit holder has a tube having a first end portion and an opposite, second end portion, a cut formed longitudinally on the tube, and a plurality of holes formed on the tube.

In one embodiment, the cut is formed substantially extending from the first end to the second end of the tube, or vice versa. The plurality of holes has three pairs of holes, where the three pairs of holes are formed substantially parallel to each other and substantially apart from each other in 120°, as seen from the longitudinal, central axis A of the tube. In operation, a replacement heart valve is mounted to the heart valve holder, a thread is guided through each of the three pair of holes, and two corresponding threads from each side for each of the three pair of holes are tied.

Additionally, a plurality of round edges are formed around the first end and the second end of the tube. The tube is made from a bio-compatible material. In one embodiment, the tube is made from an at least partially transparent material. For example, the tube can be made from a plastic.

In another aspect, the present invention relates to a replacement heart valve device. In one embodiment, the replacement heart valve device includes a heart valve holder or conduit holder formed in the form of a cylindrical tube having a first end and an opposite, second end. The cylindrical tube has a cut formed longitudinally and extending substantially from the first end to the second end of the cylindrical tube, or vice versa. The replacement heart valve device further includes a heart valve comprising a conduit that has a first end portion, an opposite, second end portion, and a plurality of cusps formed axially extending inwardly from one of the first and second end portions. In one embodiment, at least a portion of the conduit is formed with a single layer of the elastic material. In another embodiment, at least a portion of the conduit is formed with two layers of the elastic material. The heart valve is mounted onto the heart valve holder or conduit holder to be used in an operation. In one embodiment, the conduit is formed with a tubular segment of intestinal tissue extracted from a human being or animal. The heart valve holder or conduit holder is formed with a bio-compatible material.

In yet another aspect, the present invention relates to a method of making a replacement heart valve that is implantable to a patient. In one embodiment, the method includes the steps of providing a conduit that has a first end portion, an opposite, second end portion, an interior surface, an exterior surface and a diameter $d_1$, and a plurality of cusps formed axially extending inwardly from the first end portion; and providing a stent that has a first end, an opposite, second end, and a body portion defines a cavity, wherein the body portion is formed with a netted structure. The method further includes the steps of receiving the conduit into the cavity of the stent such that the stent is positioned between the first end portion and the second end portion of the conduit with the first end of the stent closer to the first end portion of the conduit than the second end of the stent to the second end portion of the conduit; attaching the first end of the stent and the first end portion of the conduit to each other; attaching the second end of the stent to the conduit; pulling the second end portion of the conduit inside-out towards to the first end portion of the conduit such that the stent is entirely covered by the corresponding portions of the conduit; and attaching the second end portion of the conduit to the first end portion of the conduit to each other to form a replacement heart valve.

In one embodiment, the conduit is formed of an elastic material.

In one embodiment, the stent formed with a netted structure is a self-expanding stent.

In one embodiment, the step of attaching the first end of the stent and the first end portion of the conduit to each other comprises the step of suturing them together, wherein the sewing is performed with 7-0 or 6-0 prolene.

In one embodiment, the step of attaching the second end of the stent to the conduit comprises the step of suturing them together, wherein the sewing is performed with 7-0 or 6-0 prolene.

In one embodiment, the step of attaching the second end portion of the conduit to the first end portion of the conduit to each other to form a replacement heart valve comprises the step of suturing them together, wherein the sewing is performed with 7-0 or 6-0 prolene.

The sewing can also be performed with string(s) made from other materials.

In a further aspect, the present invention relates to a replacement heart valve implantable in a patient. In one embodiment, the replacement heart valve includes a stent that has a first end, an opposite, second end, and a body portion defines a cavity, wherein the body portion is formed with a netted structure; a conduit formed with a tubular segment of an elastic material, wherein the conduit has a first end portion and an opposite, second end portion; and a plurality of cusps formed axially extending inwardly from one of the first and second end portions, wherein a portion of the conduit is received in the cavity of the stent, and one of the first end portion and the second end portion of the conduit is pulled inside-out towards to and attached to another of the first end portion and the second end portion of the conduit such that the stent is entirely covered by the corresponding portions of the conduit.

In one embodiment, the plurality of cusps comprises three cusps formed apart from each other.

In one embodiment, the stent formed with a netted structure is a self-expanding stent.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein:

FIG. 1D1 shows schematically a side view of the replacement heart valve that has a conduit at least partially with a single layer of the elastic material as shown in FIG. 1D, where three valve cusps are in a closed position, each with a stitch on its edge.

FIGS. 6A-6C show images of an exemplary replacement heart valve having a stent made according to the embodiment of the present invention as shown in FIGS. 5A-5E: (6A)

showing a conduit is received through the cavity of a self-expanding stent 620; (6B) showing one end portion of the conduit is folded inside-out towards another end portion of the conduit to enclose the self-expanding stent therein; and (6C) showing a perspective view of the replacement heart valve with a self-expanding stent contained therein.

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The description will be made as to the embodiments of the present invention in conjunction with the accompanying drawings of FIGS. 1-6. In accordance with the purposes of this invention, as embodied and broadly described herein, this invention, in one aspect, relates to a replacement heart valve and a method of making same.

Figure 1A:
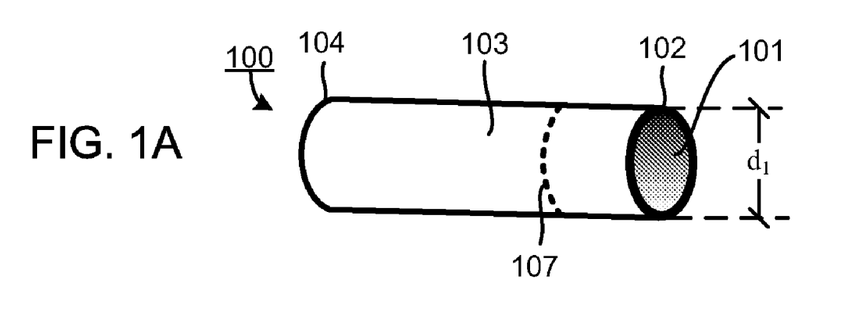
FIGS. 1A-1D show schematically a replacement heart valve in conjunction with a procedure of making same according to one embodiment of the present invention: (1A) showing a tubular segment of an elastic material, (1B) showing the tubular segment of the elastic material having a first end portion folded inside out towards to the second end portion to form a new first end portion, (1C) showing the tubular segment of the elastic material having a plurality of cusps formed at the new first end portion, and (1D) showing a tubular segment of the elastic material completely inverted inside out to form a replacement heart valve that has a conduit at least partially with a single layer of the elastic material.

Referring first to FIGS. 1A-1D, a procedure/method of making a replacement heart valve is shown according to one embodiment of the present invention. The method includes the following steps. At first, a tubular segment 100 of an elastic material is obtained from a human beings or animal, which is used to make a conduit. Suitable elastic material to practice the present invention can be one of an intestinal tissue obtained from a mammalian abdomen, a man-made bio-compatible tissue, and a polymeric material. For certainty and to help readers comprehend the invention, a tubular segment 100 of an intestinal tissue is chosen as an exemplary example. As shown in FIG. 1A, the tubular segment 100 has a first end portion 102 and an opposite, second end portion 104, an interior surface 101, an exterior surface 103 and a diameter $d_1$. The tubular segment 100 of intestinal tissue in one embodiment is obtained from a mammalian abdomen. For example, the intestinal tissue can be extracted from the patient who receives the replacement heart valve. Alternatively, the intestinal tissue can be extracted from other human beings or animals. Other types of suitable tissues may also be used to practice the present invention.

Figure 1B:
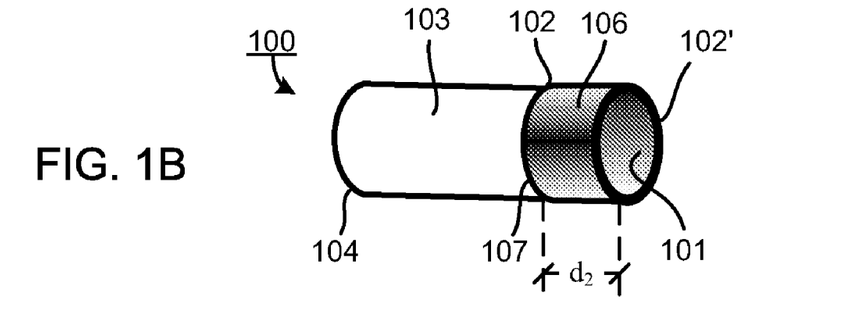

Next, the first end portion 102 of the tubular segment 100 is folded inside-out towards to the second end portion 104 of the tubular segment 100 such that the first end 102 of the tubular segment 100 reaches a position 107 on the exterior surface 103. As a result, the tubular segment 100 has a new first end 102' formed therein, as shown in FIG. 1B. The first end 102 and the new first end 102' of the tubular segment 100 define a new first end portion 106 with an axial distance $d_2$ along the length of the tubular segment 100, which is substantially equals to $d_1$, as shown in FIG. 1B.

Figure 1C:
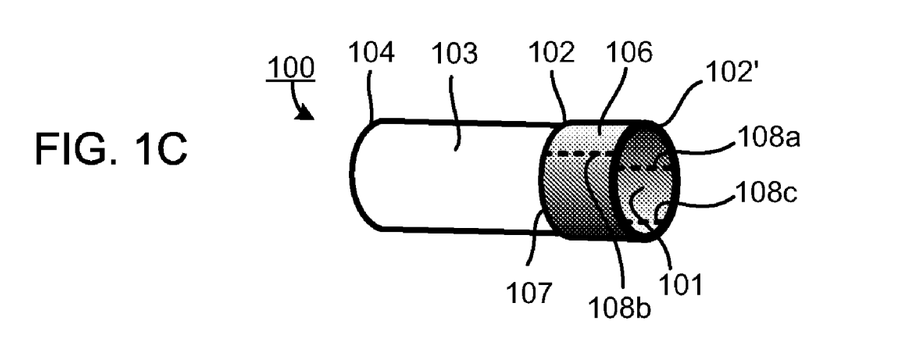

As shown in FIG. 1C, a plurality of cusps 108 is axially formed on the new first end portion 106 of the tubular segment 100. In this exemplary embodiment, three cusps 108a, 108b, and 108c are formed axially along the new first end portion 106 of the tubular segment 100, by sewing longitudinally along three lines 108a, 108b, and 108c on the new first end portion 106. The cusps 108a, 108b, and 108c are formed substantially parallel to each other and substantially apart from each other. Each cusp is separated from the other cusps by about 120°, viewed from a longitudinal, central axis of the tubular segment 100. The sewing can be performed, for example, with one or more threads of 7-0 or 6-0 prolene. Strings made with other proper materials can also be utilized.

Figure 1D:
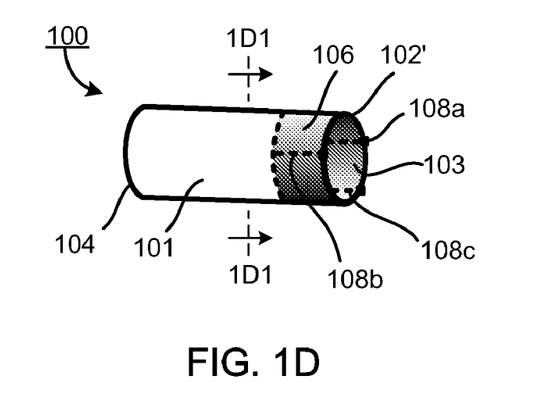
Figure 1D:
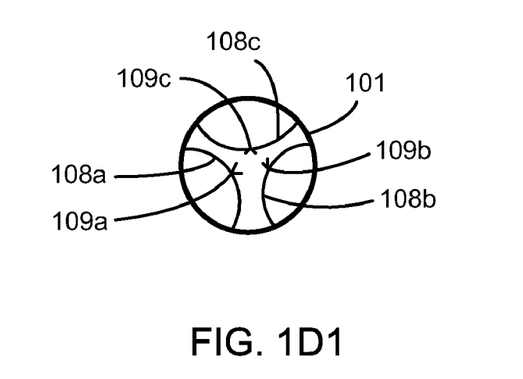

Then, the tubular segment 100 is inverted completely inside-out so that the exterior surface 103 of the tubular segment 100 and the interior surface 101 of the tubular segment 100 exchange their geometric positions, as shown in FIG. 1D. In relation to the tubular segment 100 as shown in FIG. 1B, the second end portion 104 has been inverted inside-out towards to the new first end 102', such that the second end 104 substantially reaches the new first end 102'. Accordingly, the exterior surface 103 and the interior surface 101 of the tubular segment 100 shown in FIG. 1B have exchanged their respective geometric positions to consequently become the interior surface 103 and the exterior surface 101, respectively. Dashed reference lines are also shown, which are corresponding to cusps 108a, 108b, and 108c at the new first end 102'. A replacement heart valve that has a conduit at least partially with a single layer of intestinal tissue is now formed. More specifically, the new first end portion 106 of the conduit has two layers of intestinal tissue, and the other portions of the conduit has a single layer of intestinal tissue. When such a replacement heart valve that has a conduit at least partially with a single layer of intestinal tissue is implanted in a patient's heart, body fluid such as blood will mainly flow through the portions of the conduit that has a single layer of intestinal tissue.

FIG. 1D1 shows schematically a side view of the replacement heart valve shown in FIG. 1D, where three valve cusps 108a, 108b, and 108c are in a closed position, each with a corresponding stitch (109a, 109b or 109c) on its edge. In the embodiment, each stitch (109a, 109b or 109c) is positioned substantially on the middle of the edge of a corresponding valve cusp (108a, 108b, or 108c).

Figure 1E:
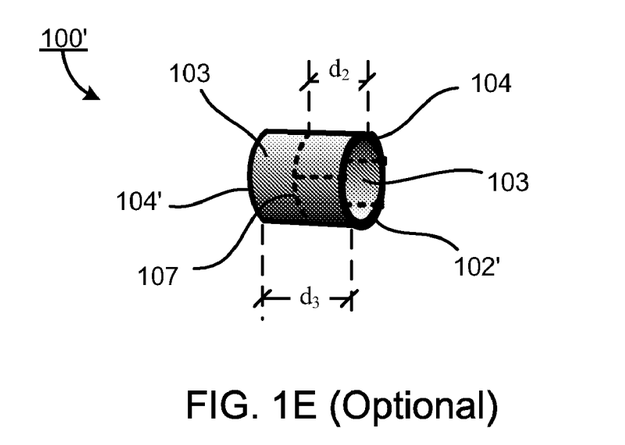
FIG. 1E shows schematically a replacement heart valve in conjunction with a procedure of making same according to another embodiment of the present invention, following the steps shown in FIGS. 1A-1D: a replacement heart valve has a conduit at least partially with two layers of the elastic material.

FIG. 1E shows schematically a replacement heart valve in conjunction with a procedure of making same according to another embodiment of the present invention, following the steps shown in FIGS. 1A-1D: the second end portion 104 of the tubular segment 100 is folded inside-out towards to the new first end 102' such that the second end 104 of the tubular segment 100 substantially reaches the new first end 102'. As a result, a replacement heart valve has a conduit 100' at least partially with two layers of intestinal tissue is formed with the new first end 102' and a new second end 104', as shown in FIG. 1E. The new first end 102' and the new second end 104' of the conduit 100' define an axial distance $d_3$ that is no smaller than either of $d_1$ and $d_2$. As formed, the portion between the new first end 102' and the position 107 of the conduit has three layers of intestinal tissue, and the other portion of the conduit has two layers of intestinal tissue. When such a replacement heart valve that has a conduit at least partially with two layers of intestinal tissue is implanted in a patient's heart, body fluid such as blood will mainly flow through the portions of the conduit that has two layers of intestinal tissue Both a replacement heart valve that has a conduit at least partially with a single layer of intestinal tissue and a replacement heart valve that has a conduit at least partially with two layers of intestinal tissue can be mounted to a conduit holder that is described below.

Figure 2A:
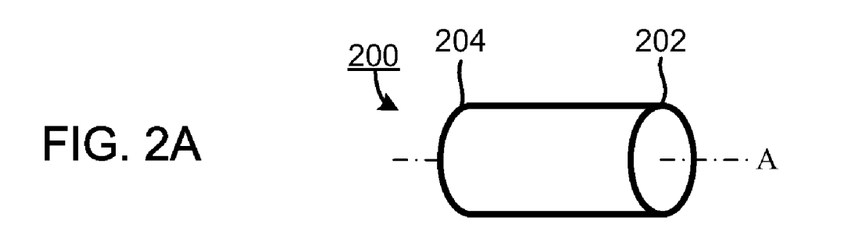
FIGS. 2A-2F show schematically a heart valve holder or conduit holder in conjunction with a procedure of making same according to one embodiment of the present invention, (2A) showing a cylindrical tube, (2B) showing the cylindrical tube having a longitudinal cut, (2C) showing the cylinder having a plurality of smoothly rounded edges formed at the junctions of the longitudinal cut and the two end of the cylindrical tube, (2D) and (2E) showing the conduit holder having a plurality of holes formed in the cylindrical tube, and (2F) showing a top view of the heart valve holder or conduit holder.

Referring to FIGS. 2A-2E, a procedure/method of making a heart valve holder or conduit holder usable for mounting a replacement heart valve is shown according to one embodiment of the present invention. The method includes the step of providing a tube 200 having a first end portion 202 and an opposite, second end portion 204, as shown in FIG. 2A. The tube 200 is made from a bio-compatible material. In one embodiment, the tube 200 is made from an at least partially transparent material. For example, the tube 200 can be made from a transparent plastic.

Then, a cut 210 is formed longitudinally on the tube 200. The cut 210 substantially extends from the first end 202 to the second end 204 or vice versa, as show in FIG. 2B. After the cut 210 is formed, round edges 212a, 212b, 214a and 214b are formed around the first end 202 and the second end 204 of the cut tube 200. Furthermore, a plurality of holes is formed on the cut tube 200, thereby forming a conduit holder 200'. In the embodiment as shown in FIGS. 2D and 2E, the plurality of holes formed on the cut tube 200 has three pairs of holes 216a, 216b and 216c. Each pair of holes is axially aligned. The three pairs of holes 216a, 216b and 216c are formed substantially parallel to each other and substantially apart from each other in about 120°, viewed from a longitudinal, central axis A of the conduit holder 200', as shown in FIG. 2F. These holes are adapted for guiding a thread through each of the three pair of holes, where two corresponding threads from each side for each of the three pair of holes are tied. Such a heart valve holder can be utilized to facilitate the medical procedure for implanting a replacement heart valve. Threads of 7-0 or 6-0 prolene can be used to practice the present invention.

Figure 3:
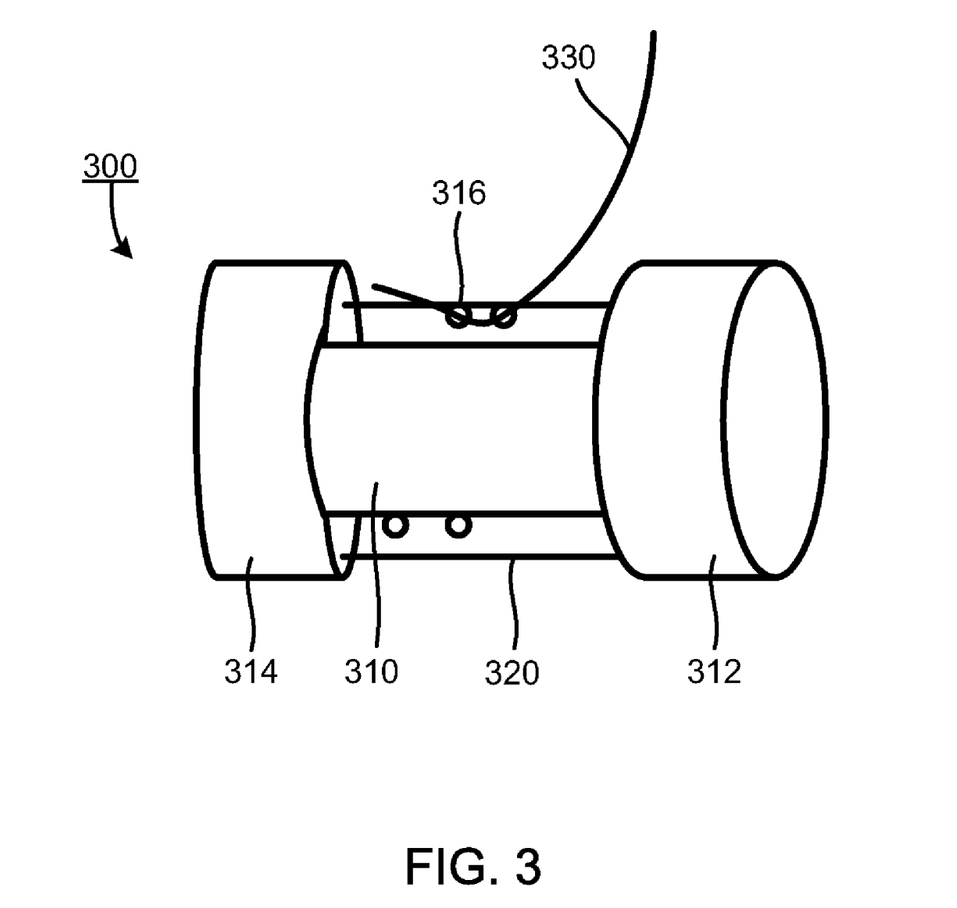
FIG. 3 shows schematically a replacement heart valve device according to one embodiment of the present invention.

FIG. 3 shows schematically a replacement heart valve device 300 having a conduit holder 320 and a conduit 310. The conduit 310 can be one of a conduit at least partially with a single layer of intestinal tissue as shown in FIG. 1D and a conduit at least partially with two layers of intestinal tissue as shown in FIG. 1E. The conduit holder 320 has a plurality of pairs of holes 316 formed thereon. As assembled, the conduit 310 passes through the conduit holder 320. Each of the first and second end portions 312 and 314 of the conduit 310 is folded inside-out and attached onto a corresponding end portion of the conduit holder 320. A total of six threads are placed on the conduit. Three are placed at the one end of the conduit, at positions 108a, 108b, and 108c in FIG. 1C, respectively. Three additional threads are placed at the other end of the conduit, corresponding to positions 108a, 108b, and 108c, respectively. Then, each thread 330 is guided through each pair of holes, and two corresponding ends of the thread 330 passing through the pair of holes are tied together. Such a replacement heart valve device 300 allows a fluid to flow through the conduit 310 from one end of the replacement heart valve device 300 to the other end of replacement heart valve device 300, or vice versus, and to allow easy use in a medical procedure for a heart valve replacement by medical professionals. Once the conduit 310 properly replaces a defective valve of a patient, the conduit holder 320 can be easily disengaged from the conduit 310 and removed from the patient's heart.

Figure 5A:
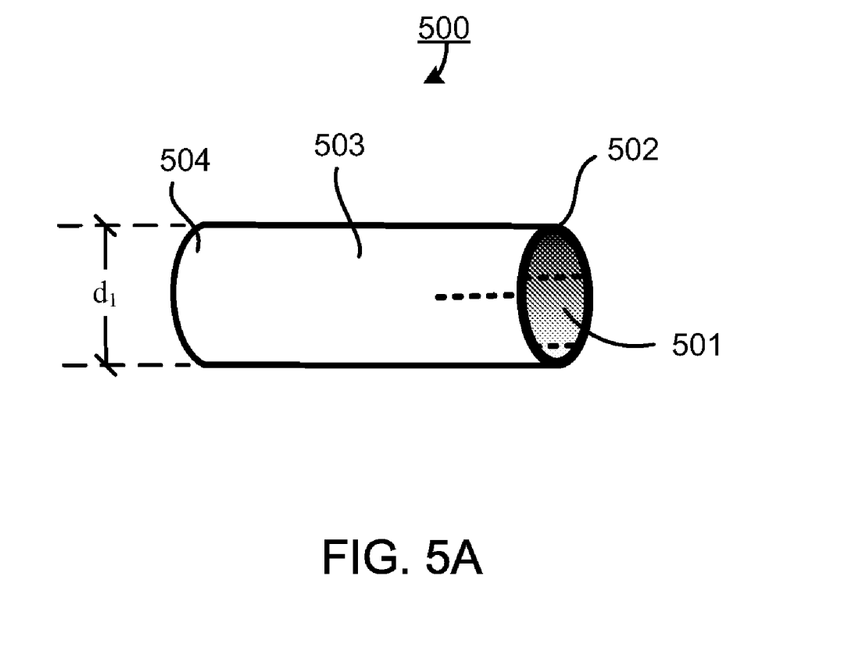
FIGS. 5A-5E show schematically a replacement heart valve having a stent such as a self-expanding stent in conjunction with a procedure of making same according to one embodiment of the present invention: (5A) showing a heart valve conduit made in conjunction with a procedure of making same according to one embodiment of the present invention as shown in FIGS. 1A-1D is provided; (5B) showing the heart valve conduit is partially placed inside a self-expanding stent. The length of the conduit is at least twice as long as that of the stent; (5C) and (5D) showing that the stent is attached to the heart valve conduit at a proper configuration; and (5E) showing that one half of the heart valve conduit outside of the stent is pulled towards to the other end of the heart valve conduit inside-out, and that both ends of the heart valve conduit are attached and sewn to form a replacement heart valve with a stent inside.

Referring now to FIGS. 5A-5E, a procedure/method of making a replacement heart valve is shown according to yet another aspect of the present invention. The method includes the following steps. In one embodiment, as shown in FIG. 5A, a conduit 500 is provided that has a first end portion 502, an opposite, second end portion 504, an interior surface 501, an exterior surface 503 and a diameter $d_1$, and a plurality of cusps 508a, 508b, 508c formed axially extending inwardly from the first end portion 502. In one embodiment, the conduit 500 is at least partially with a single layer of intestinal tissue as shown in FIG. 1D and formed according to the procedure described above in connection with FIGS. 1A-1D. Other types of conduit can also be utilized to practice the present invention.

Figure 5B:
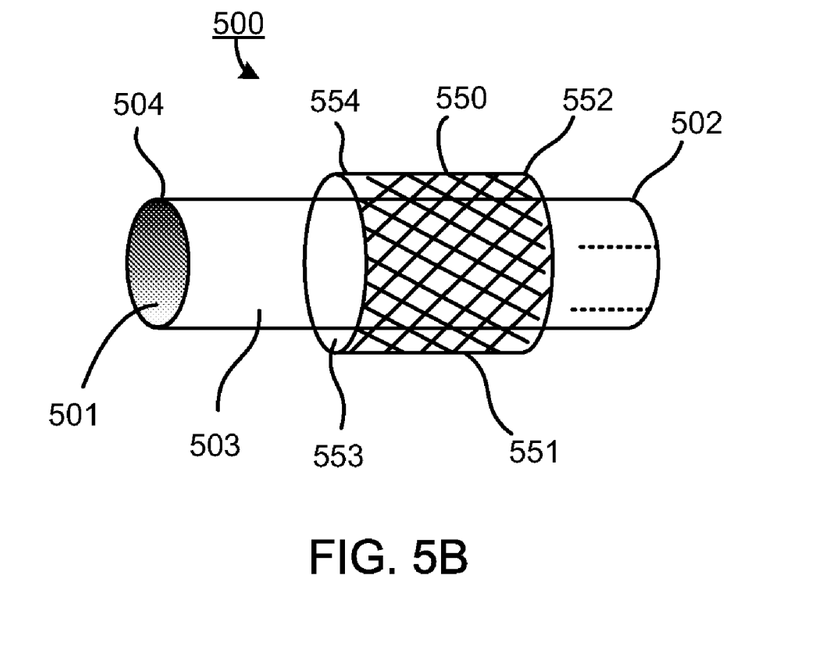

As shown in FIG. 5B, a stent 550 is also provided that has a first end 552, an opposite, second end 554, and a body portion 551 defines a cavity 553, wherein the body portion 551 is formed with a netted structure. In one embodiment, the length of the conduit 500 is at least twice as long as that of the stent 550. In one embodiment, the stent 550 formed with a netted structure is a self-expanding stent. Examples of self-expanding stents that can be utilized to practice the present invention are RX Acculink® Carotid stent with 10.0 mm diameter, Model Number 1011342-30, made by Abbott Vascular of Redwood City, Calif., WALLSTENT® colonic and duodenal Endoprosthesis with 22.0 mm diameter), Model Number M00565640, made by Boston Scientific of Boston, Mass., and Polyflex Airway® stent with 22.0 mm diameter, Model Number M00570320, made by Boston Scientific of Boston, Mass. Other types of self-expanding stents can also be utilized.

In these examples, Acculink® stent is made of nitinol, WALLSTENT® stent is made of metal, and Polyflex Airway® stent is made of silicone. As further described and set forth infra, a replacement heart valve with stent according to the present invention has a unique feature that substantially whole stent, both inside and outside, is covered with an elastic material, here the intestinal tissue, no part of the stent is exposed to body fluid such as blood. Therefore, the material of the stent will not be an issue at least for host- or bio-compatibility. Rather, which stent is chosen will be a matter of ease of use.

Next, as shown in FIG. 5B, the conduit 500 is received into the cavity of the stent 550 such that the stent 550 is positioned between the first end portion 502 and the second end portion 504 of the conduit 500 with the first end 552 of the stent 550 closer to the first end portion 502 of the conduit 500 than the second end 554 of the stent 550 to the second end portion 504 of the conduit 500.

Figure 5C:
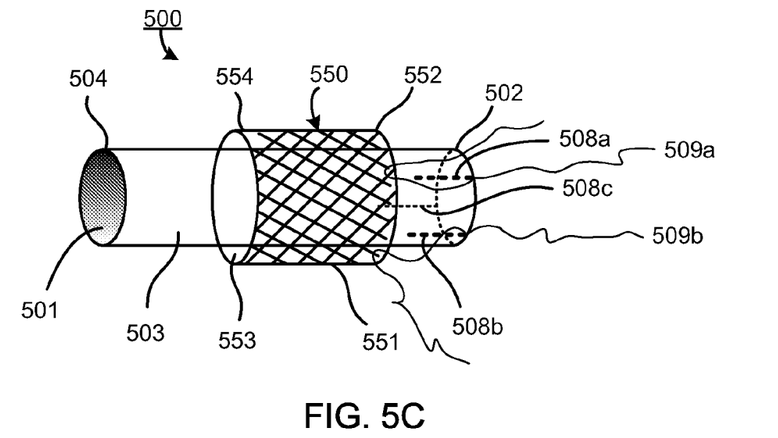

Then, the first end 552 of the stent 550 and the first end portion 502 of the conduit 500 are attached to each other. In one embodiment as shown in FIG. 5C, the first end 552 of the stent 550 and the first end portion 502 of the conduit 500 are attached to each other by suturing them together, wherein the sewing is performed with 7-0 or 6-0 prolene. For examples, three 6-0 prolene threads 509a, 509b and 509c are used to suture the first end portion 502 of the conduit 500 through three corresponding commissures 508a, 508b, and 508c, respectively to the stent 550 through corresponding net structure of the stent 550.

Figure 5D:
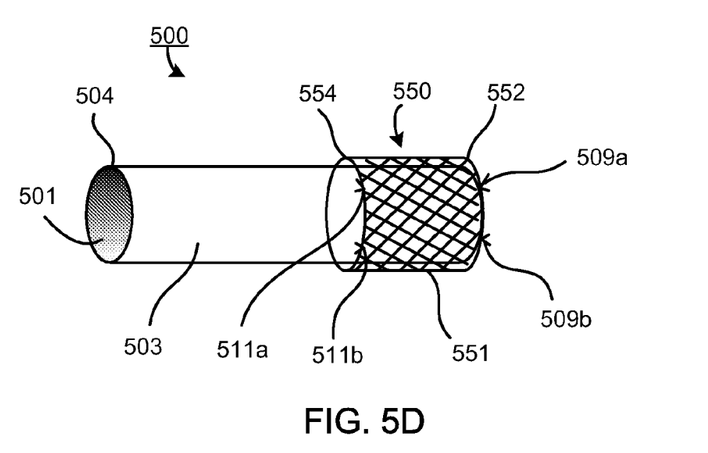

Furthermore, the second end 554 of the stent is attached to the conduit 500. In one embodiment, the step of attaching the second end 554 of the stent 550 to the conduit 500 comprises the step of suturing them together, wherein the sewing is performed with 7-0 or 6-0 prolene. For example, three additional 6-0 prolene threads (only two, 511a and 511b are shown) are placed in the corresponding positions of the conduit 500 to attach it to the second end 554 of the stent 550, as shown in FIG. 5D.

Figure 5E:
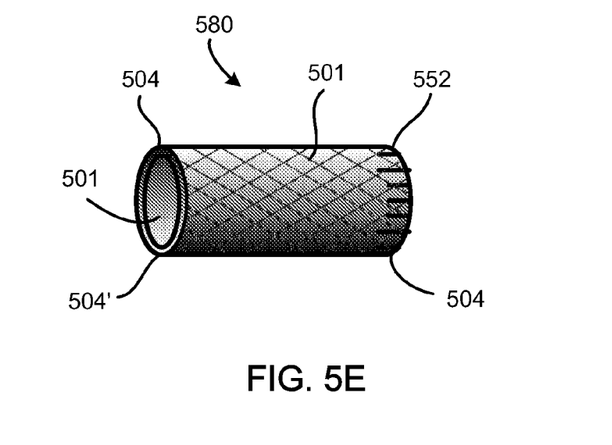

Next, referring now to FIG. 5E, the second end portion 504 of the conduit 500 is pulled inside-out towards to the first end portion 502 of the conduit 500 such that the stent 550 is entirely covered by the corresponding portions of the conduit 500. Then, the second end portion 504 of the conduit 500 to the first end portion 502 of the conduit 500 are attached to each other to form a replacement heart valve 580. In one embodiment, the second end portion 504 of the conduit 500 to the first end portion 502 of the conduit 500 are attached to each other by suturing them together, wherein the sewing is performed with 7-0 or 6-0 prolene. Such a replacement heart valve 580 can be used in a percutaneous heart valve implantation for a patient.

The sewing can also be performed with string(s) made from other materials.

In a further aspect, the present invention relates to a replacement heart valve 580 implantable in a patient. In one embodiment, the replacement heart valve 580 includes a stent 550 that has a first end 552, an opposite, second end 554, and a body portion 551 defines a cavity 553, wherein the body portion 551 is formed with a netted structure. The replacement heart valve 580 further includes a conduit 500 formed with a tubular segment of intestinal tissue, wherein the conduit has a first end portion 502 and an opposite, second end portion 504, and a plurality of cusps formed axially extending inwardly from one of the first and second end portions, wherein a portion of the conduit 500 is received in the cavity 553 of the stent 550, and one of the first end portion 502 and the second end portion 504 of the conduit 500 is pulled inside-out towards to and attached to another of the first end portion 502 of the conduit 500 such that the stent 550 is entirely covered by the corresponding portions of the conduit 500.

In one embodiment, the plurality of cusps comprises three cusps 108a, 108b and 108c formed apart from each other.

In one embodiment, the stent 550 formed with a netted structure is a self-expanding stent.

In one embodiment, the conduit 500 is one that is at least partially with a single layer of intestinal tissue as shown in FIG. 1D and formed according to the procedure described above in connection with FIGS. 1A-1D. Other types of conduit can also be utilized to practice the present invention.

Examples of the Invention

Without intent to limit the scope of the invention, additional exemplary methods and their related results according to the embodiments of the present invention are given below. Note that titles or subtitles may be used in the examples for convenience of a reader, which in no way should limit the scope of the invention.

Each example below is practiced according to at least one aspect of the present invention.

Preparing Small Intestine Submucosa (SIS) Material: In this exemplary embodiment, a section of small intestine (about 30 cm long) was harvested under general anesthesia. The freshly resected section was washed and mechanically delaminated of the superficial layers of the tunica mucosa and the entire tunica muscularis externa for about 20 minutes, while the intestine maintained its cylindrical shape. The resected section was placed in a container with about 150 ml of $dH_2O$ for about 4 hours with continuous rocking. A complete water change occurred each hour. The section was then placed in about 300 ml of about 0.01% peracetic acid in sterilized phosphate buffered saline solution with continuous rocking for about 20 hours.

Afterwards, the section of small intestine was placed in a container with about 200 ml volume of sterilized phosphate buffered saline solution for about 4.5 hours with continuous rocking. A complete solution change occurred at least 10 times. Finally, the section was placed in a final sterile PBS with the container tightly sealed, and kept refrigerated.

Preparing a Right Ventricular Outflow Tract Conduit: As shown in FIG. 1B, the first end 102 of the SIS tubular 100 was folded inside-out towards the second end 104 of the SIS tubular 100 to form a folding portion 106 between the first end 102 and a new first end 102' of the SIS tubular 100. The length, $d_2$, of the folding portion 106 substantially equals to the diameter, $d_1$, of the SIS tubular 100. As shown in FIG. 1C, three longitudinal lines 108a, 108b and 108c were sewn with a thread of 7-0 or 6-0 prolene to produce three cusps accordingly. Each cusp is apart from the other two cups by 120 degrees.

The SIS tubular 100 was inverted completely inside-out, as shown in FIG. 1D. Then, the second end 104 of the SIS tubular 100 was folded inside-out towards the new first end 102', thereby forming a conduit 100' having a double-layer wall, as shown in FIG. 1E.

Preparing a Right Ventricular Outflow Tract Conduit with a Valve Holder: In the exemplary embodiment as shown in FIGS. 2A-2E, a thin cylindrical tube 200 with a diameter of about 3 cm and a length of about 3 cm was utilized to form a conduit holder. The thin cylindrical tube 200 is made of clear polycarbonate tube lamp guard, TGT8 CL, (Lithonia Lighting, Conyers, Ga.).

Figure 2B:
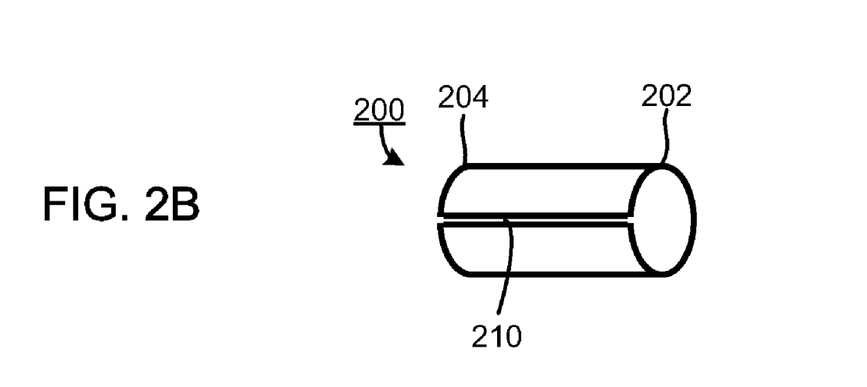
Figure 2C:
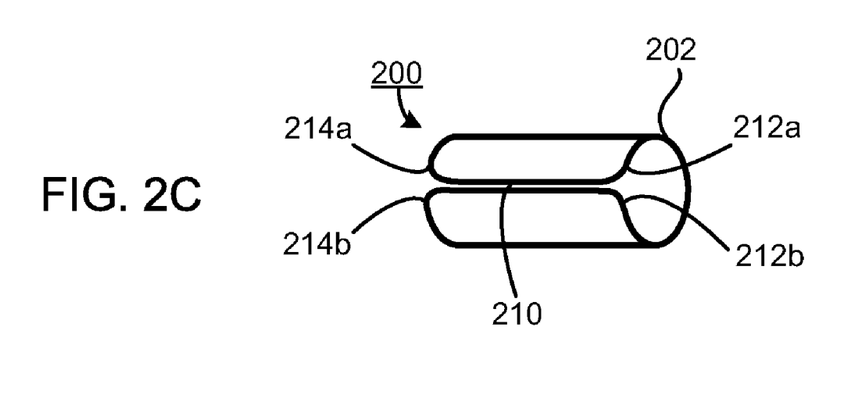
Figure 2D:
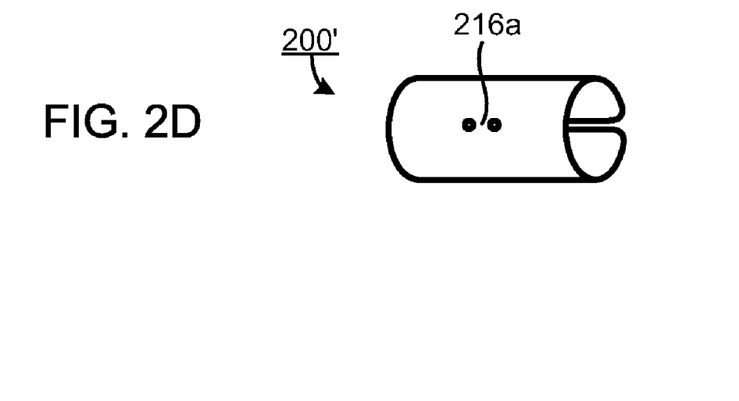
Figure 2E:
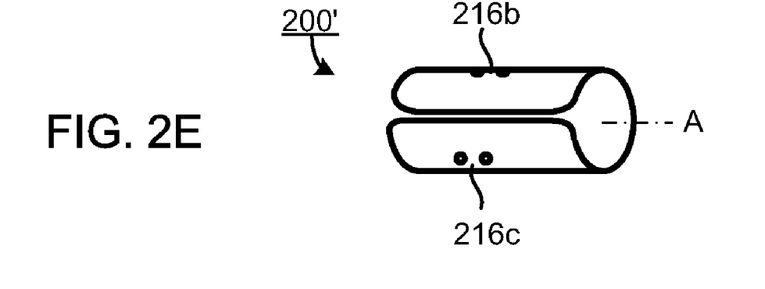
Figure 2F:
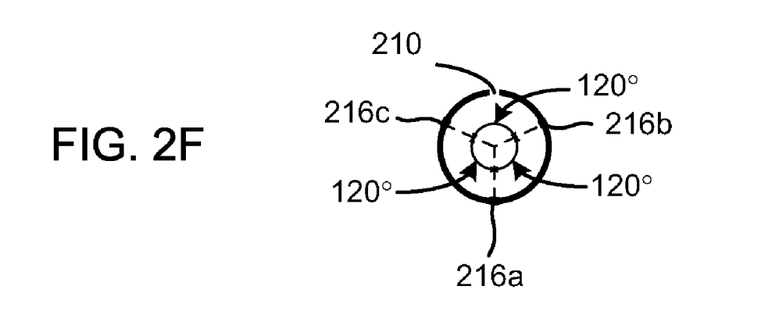

The cylindrical tube 200 was then cut longitudinally to form a cut 210 that extends from one end to the other end of the cylindrical tube 200, as shown in FIG. 2B. Four edges 212a-212d at the junctions of the cut 210 and the first and second ends 202 and 204 of the cylindrical tube 200 were smoothly rounded, as shown in FIG. 2C. Furthermore, three pairs of holes 216a, 216b and 216c were formed on the cylindrical tube 200, with each pair of holes aligned axially and being apart from the others by about 120° viewed from the longitudinal, central axis A of the tube 200, thereby by forming a conduit holder 200', as shown in FIGS. 2D-2F. The size of each hole was adapted so that a thread/needle of 7-0 or 6-0 prolene could pass through therefrom.

Referring back to FIG. 3, the replacement heart valve device 300 has a conduit holder 320 and a conduit 310. The conduit 310 is attached onto the conduit holder 320, where a thread 330 of 7-0 or 6-0 prolene is guided through each pair of holes of the conduit holder 320. Two corresponding ends of the thread 330 passing through the pair of holes are tied together.

Figure 4A:
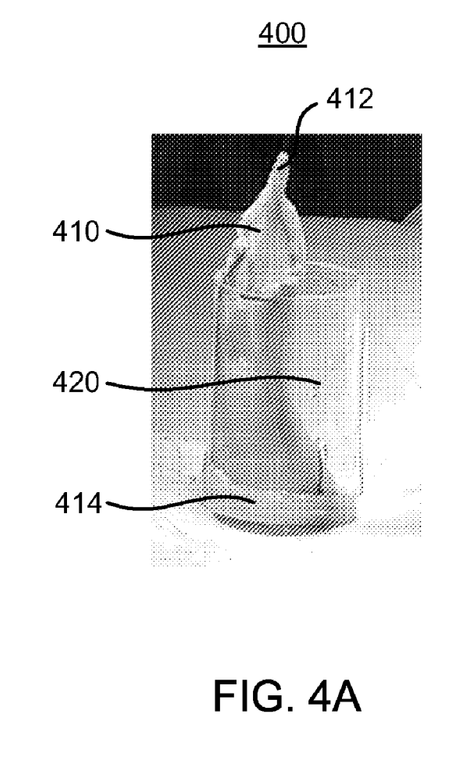
FIGS. 4A-4C show images of a replacement heart valve device according to one embodiment of the present invention: (4A) showing a replacement heart valve passing through a conduit holder, (4B) showing each of the first and second end portions of the replacement heart valve is folded inside-out and attached onto a corresponding end portion of the conduit holder, and (4C) showing a perspective view of the replacement heart valve mounted onto the conduit holder.
Figure 4B:
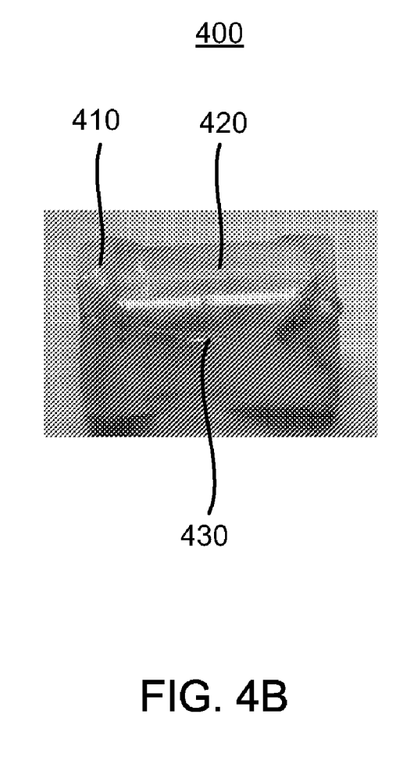
Figure 4C:
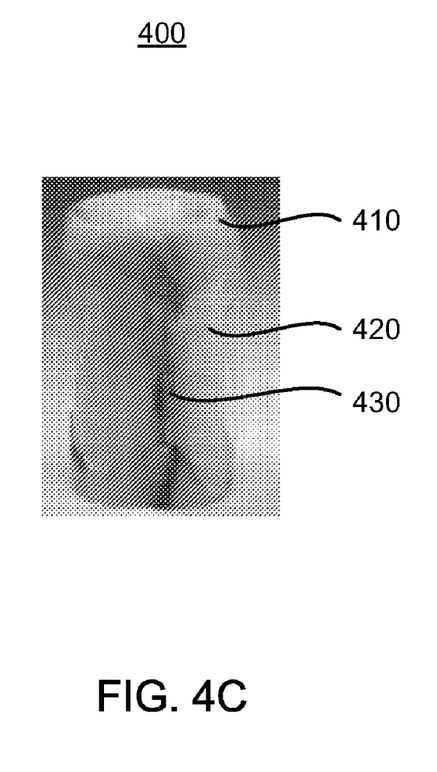

FIG. 4 shows a replacement heart valve device 400. At first, a conduit 410 is passed through the conduit holder 320, as shown in FIG. 4A. Next, each of the first and second end portions 412 and 414 of the conduit 410 is folded inside-out and attached onto a corresponding end portion of the conduit holder 420. Then, a 7-0 or 6-0 prolene suture was placed on three commissures on both sides, i.e., a thread 430 of 7-0 or 6-0 prolene is guided through each pair of holes, and two corresponding ends of the thread 430 passing through the pair of holes are tied together, as shown in FIGS. 4B and 4C. The replacement heart valve device 400 can be used in a surgical procedure for replacement of a defective heart valve of patient.

Figure 6A:
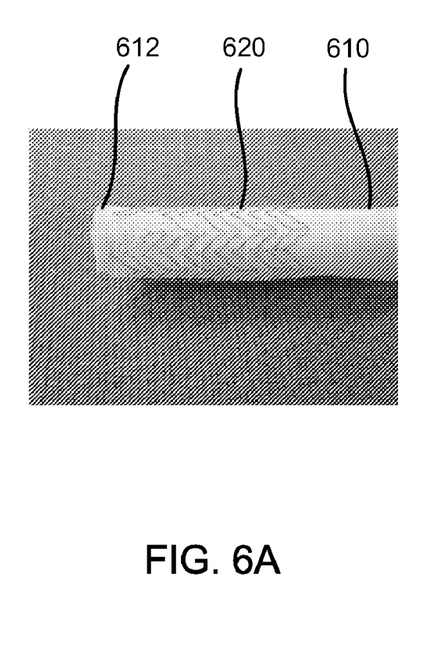
Figure 6B:
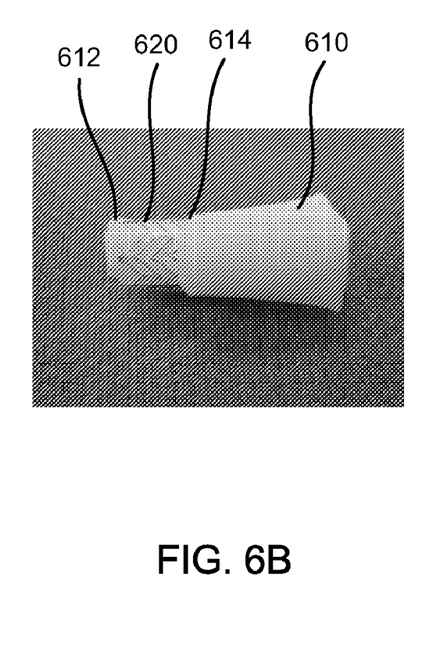
Figure 6C:
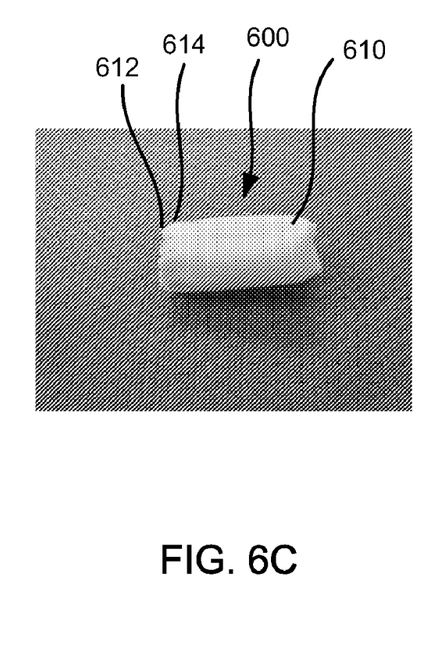

Preparing a Right Ventricular Outflow Tract Conduit with a self-expanding stent for percutaneous implantation: In the exemplary embodiment as shown in FIGS. 6A-6C, a self-expanding stent with a diameter of 1.0 cm and a length of about 3 cm was utilized. A rubber cylindrical tube with a diameter of about 1.0 cm and a length of about 6 cm was utilized as a conduit candidate to show how a conduit is mounted onto the stent. At first, a conduit 610 is received through the cavity of a self-expanding stent 620, as shown in FIG. 6A. As shown in FIG. 6B, one end portion 614 of the conduit 610 is folded inside-out towards another end portion 612 of the conduit 610 to enclose the self-expanding stent 620 therein. Then, as shown in FIG. 6C, the end portion 614 and the end portion 612 of the conduit are attached together, here tied together through sewing, to form a replacement heart valve 600 that can be used as, for example, a right ventricular outflow tract conduit with a self-expanding stent for percutaneous implantation.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims, the drawings.

What is claimed is:

1. A replacement heart valve implantable in a patient, comprising:
   (a) a conduit formed with a tubular segment of an elastic material, wherein the conduit has a first end portion at a first end, an opposite, second end portion at a second end, an interior surface, an exterior surface, a longitudinal axis, and a diameter $d_1$, and wherein a new first end portion is formed from the first end portion that is folded inside-out towards the second end portion such that the first end of the tubular segment reaches a position on the exterior surface; and
   (b) a plurality of cusps formed axially on and extending inwardly from the new first end portion along the longitudinal axis of the conduit, wherein each of the plurality of cusps has a corresponding line of one or more threads sewn longitudinally on the new first end portion, wherein the new first end portion has an axial distance $d_2$ along the longitudinal axis of the conduit that is substantially equal to $d_1$, and wherein the conduit is formed from the tubular segment with the cusps that have been formed on the new first end portion, which is folded inside-out such that the exterior surface of the tubular segment and the interior surface of tubular segment exchange their geometric positions.

2. The replacement heart valve of claim 1, wherein the elastic material is one of an intestinal tissue obtained from a mammalian abdomen, a man-made bio-compatible tissue, and a polymeric material.

3. The replacement heart valve of claim 2, wherein the intestinal tissue is extracted from a patient who receives the replacement heart valve.

4. The replacement heart valve of claim 1, wherein the plurality of cusps comprises three cusps.

5. The replacement heart valve of claim 4, wherein the three cusps are formed substantially apart from each other in 120°, as seen from a longitudinal, central axis of the conduit.

6. The replacement heart valve of claim 2, wherein at least a portion of the conduit is formed with a layer of intestinal tissue.

7. The replacement heart valve of claim 2, wherein at least a portion of the conduit is formed with two layers of intestinal tissue.

8. A replacement heart valve device, comprising:
   (a) a heart valve holder or conduit holder formed in the form of a cylindrical tube having a first end and an opposite, second end; and
   (b) a heart valve comprising a conduit formed from a tubular segment of an elastic material that has a first end, an opposite, second end, an interior surface, an exterior surface, and a longitudinal axis, and wherein a new first end portion is formed from the first end that is folded inside-out towards the second end such that the first end of the cylindrical tube reaches a position on the exterior surface, and wherein a plurality of cusps are formed axially on and extend inwardly from the new first end portion along the longitudinal axis of the conduit, wherein in operation, the heart valve is mounted onto the heart valve holder or conduit holder.

9. The replacement heart valve device of claim 8, wherein the conduit is formed with a tubular segment of an elastic material.

10. The replacement heart valve device of claim 9, wherein at least a portion of the conduit is formed with a layer of intestinal tissue.

11. The replacement heart valve device of claim 9, wherein at least a portion of the conduit is formed with two layers of intestinal tissue.

12. The replacement heart valve device of claim 8, wherein the cylindrical tube has a cut formed longitudinally and extending substantially from the first end to the second end of the cylindrical tube, or vice versa.

13. The replacement heart valve device of claim 8, wherein the heart valve holder or conduit holder is formed with a bio-compatible material.

14. The replacement heart valve device of claim 8, wherein the heart valve holder or conduit holder is removable.

15. A replacement heart valve implantable in a patient, comprising:
   (a) a stent that has a first end, an opposite, second end, and a body portion defines a cavity, wherein the body portion is formed with a netted structure;
   (b) a conduit formed with a tubular segment of an elastic material, wherein the conduit has a first end portion and an opposite, second end portion; and
   (c) a plurality of cusps formed axially on and extending inwardly from only one of the first and second end portions, wherein a portion of the conduit is received in the cavity of the stent, and one of the first end portion and the second end portion of the conduit is pulled inside-out towards and attached to another of the first end portion and the second end portion of the conduit such that the stent is entirely covered by the corresponding portions of the conduit.

16. The replacement heart valve of claim 15, wherein the plurality of cusps comprises three cusps formed apart from each other.

17. The replacement heart valve of claim 15, wherein the stent formed with a netted structure is a self-expanding stent.

18. A replacement heart valve implantable in a patient, comprising:
   (a) a conduit formed with a tubular segment of an elastic material, wherein the conduit has a first end portion at a first end, an opposite, second end portion at a second end, an interior surface, an exterior surface, a longitudinal axis, and a diameter $d_1$, and wherein a new first end portion is formed from the first end portion that is folded inside-out towards the second end portion such that the first end of the tubular segment reaches a position on the exterior surface; and (b) a plurality of cusps formed axially on and extending inwardly from the new first end portion, wherein each of the plurality of cusps has a corresponding line of one or more threads sewn longitudinally on the new first end portion, and a stitch positioned substantially on the middle of an edge of the cusp, and wherein the new first end portion has an axial distance $d_2$ along the longitudinal axis of the conduit that is substantially equal to $d_1$, wherein the plurality of cusps are parallel to each other and parallel to the longitudinal axis of the conduit.

19. The replacement heart valve of claim 18, wherein the conduit is formed from the tubular segment with the cusps that have been formed on the new first end portion, that is folded inside-out such that the exterior surface of the tubular segment and the interior surface of tubular segment exchange their geometric positions.

\* \* \* \* \*